United States Patent
Nakatate et al.

(10) Patent No.: US 10,682,047 B2
(45) Date of Patent: Jun. 16, 2020

(54) TRACHEAL TUBE

(71) Applicant: FUJIKURA LTD., Tokyo (JP)

(72) Inventors: Kenichi Nakatate, Sakura (JP); Hitoe Iikura, Sakura (JP)

(73) Assignee: FUJIKURA LTD., Tokyo (JP)

(*) Notice: Subject to any disclaimer, the term of this patent is extended or adjusted under 35 U.S.C. 154(b) by 429 days.

(21) Appl. No.: 14/775,128

(22) PCT Filed: Oct. 21, 2013

(86) PCT No.: PCT/JP2013/078456
§ 371 (c)(1),
(2) Date: Sep. 11, 2015

(87) PCT Pub. No.: WO2014/155795
PCT Pub. Date: Oct. 2, 2014

(65) Prior Publication Data
US 2016/0030693 A1     Feb. 4, 2016

(30) Foreign Application Priority Data

Mar. 28, 2013 (JP) ................. 2013-069271

(51) Int. Cl.
*A61B 1/267* (2006.01)
*A61B 1/05* (2006.01)
(Continued)

(52) U.S. Cl.
CPC .......... *A61B 1/267* (2013.01); *A61B 1/00154* (2013.01); *A61B 1/015* (2013.01);
(Continued)

(58) Field of Classification Search
CPC ............ A61B 1/00096; A61B 1/00163; A61B 1/00165; A61B 1/00167; A61B 1/0017;
(Continued)

(56) References Cited

U.S. PATENT DOCUMENTS 4,272,156 A * 6/1981 Ishibashi ............ A61B 1/00117
385/117
2008/0114207 A1* 5/2008 Krupa ................ A61B 1/00068
600/178
(Continued)

FOREIGN PATENT DOCUMENTS

EP   2 011 428 A1   1/2009
JP   08-322937 A   12/1996
(Continued)

OTHER PUBLICATIONS

International Preliminary Report on Patentability dated Oct. 8, 2015 issued by the International Bureau in counterpart International Application No. PCT/JP2013/078456.
(Continued)

*Primary Examiner* — Ryan N Henderson
(74) *Attorney, Agent, or Firm* — Sughrue Mion, PLLC

(57) ABSTRACT

Provided is a tracheal tube that can be easily inserted into the inside of a subject and enables real-time observation of a state after tracheal intubation. The tracheal tube (1) includes a hollow tube body (2), a lumen (2a), and a scope unit (3), wherein the tube body (2) is inserted into the subject, the lumen (2a) is mounted to the tube body (2), and the scope unit (3) includes a cable portion (4) inserted in the lumen (2a) and an imaging optical system mounted to the distal end of the cable portion (4), the imaging optical system including an imaging device configured to image the inside of the subject.

9 Claims, 4 Drawing Sheets

(51) Int. Cl.
*A61B 1/07* (2006.01)
*A61B 1/00* (2006.01)
*A61B 1/06* (2006.01)
*A61B 1/24* (2006.01)
*A61M 16/04* (2006.01)
*A61B 1/015* (2006.01)

(52) U.S. Cl.
CPC ................. *A61B 1/05* (2013.01); *A61B 1/06* (2013.01); *A61B 1/07* (2013.01); *A61B 1/24* (2013.01); *A61B 1/2673* (2013.01); *A61B 1/2676* (2013.01); *A61M 16/04* (2013.01); *A61M 16/0484* (2014.02); *A61M 16/0486* (2014.02); *A61B 1/00082* (2013.01)

(58) Field of Classification Search
CPC ............ A61B 1/00172; A61B 1/00174; A61B 1/00177; A61B 1/00179; A61B 1/00181; A61B 1/00183; A61B 1/00186; A61B 1/00188; A61B 1/0019; A61B 1/00193; A61B 1/00195; A61B 1/00197; A61B 1/002; A61B 1/04; A61B 1/041; A61B 1/042; A61B 1/043; A61B 1/045; A61B 1/05; A61B 1/051; A61B 1/053; A61B 1/055; A61B 1/06; A61B 1/0607; A61B 1/0615; A61B 1/0623; A61B 1/063; A61B 1/0638; A61B 1/0646; A61B 1/0653; A61B 1/0661; A61B 1/0669; A61B 1/0676; A61B 1/0684; A61B 1/0692; A61B 1/07; A61B 1/267; A61B 1/2673; A61B 1/2676; A61B 1/24; A61M 16/04; A61M 16/0484; A61M 16/0486
USPC ........ 600/104, 106, 107, 109–112, 121–125, 600/156–181; 128/207.14, 200.26
See application file for complete search history.

(56) References Cited

U.S. PATENT DOCUMENTS

| | | | |
|---|---|---|---|
| 2009/0048490 A1 | 2/2009 | Iijima | |
| 2010/0199448 A1* | 8/2010 | Vazales | A61B 1/00082 15/104.05 |
| 2010/0249639 A1* | 9/2010 | Bhatt | A61B 1/00082 600/546 |
| 2011/0157574 A1* | 6/2011 | Kato | A61B 1/05 355/71 |
| 2012/0167882 A1* | 7/2012 | Wood | A61B 1/00082 128/204.17 |
| 2012/0172664 A1* | 7/2012 | Hayman | A61B 1/127 600/109 |
| 2012/0302833 A1* | 11/2012 | Hayman | A61B 5/061 600/120 |
| 2013/0023729 A1* | 1/2013 | Vazales | A61B 1/0669 600/104 |
| 2013/0053636 A1* | 2/2013 | Hayman | A61B 1/00082 600/104 |
| 2013/0131447 A1* | 5/2013 | Benning | A61B 1/00137 600/109 |
| 2013/0137925 A1* | 5/2013 | Ushijima | A61B 1/051 600/109 |
| 2013/0158351 A1* | 6/2013 | Daher | A61M 16/04 600/109 |
| 2013/0324798 A1* | 12/2013 | Molnar | A61M 16/04 600/120 |
| 2014/0150782 A1* | 6/2014 | Vazales | A61M 16/0463 128/202.16 |
| 2014/0275778 A1* | 9/2014 | Gunday | A61M 16/0488 600/109 |
| 2014/0288371 A1* | 9/2014 | Nakatate | A61B 1/267 600/156 |

FOREIGN PATENT DOCUMENTS

| | | |
|---|---|---|
| JP | 2000-070371 A | 3/2000 |
| JP | 2001-128929 A | 5/2001 |
| JP | 2005-329079 A | 12/2005 |
| JP | 2007-289355 A | 11/2007 |
| JP | 2011-092379 A | 5/2011 |
| JP | 2012-517270 A | 8/2012 |
| WO | 2007/122845 A1 | 11/2007 |
| WO | 2010/089726 A2 | 8/2010 |

OTHER PUBLICATIONS

International Search Report of PCT/JP2013/078456 dated Nov. 19, 2013 [PCT/ISA/210].

* cited by examiner

TRACHEAL TUBE

CROSS REFERENCE TO RELATED APPLICATIONS

This application is a National Stage of International Application No. PCT/JP2013/078456, filed Oct. 21, 2013, claiming priority based on Japanese Patent Application No. 2013-069271, filed Mar. 28, 2013, the contents of all of which are incorporated herein by reference in their entirety.

TECHNICAL FIELD

The present invention relates to a tracheal tube.

BACKGROUND ART

Tracheal intubation is a method of establishing an airway by inserting a tracheal tube from the mouth or nose through the throat to the bronchus of a subject. The tracheal intubation makes it possible to reliably maintain an airway and also prevent aspiration, and thus is used in various situations including emergency medical care.

The insertion of the tracheal tube into the subject is performed using, for example, an endoscope. In specific, first of all, the endoscope is inserted in the trachea. Thereafter, the tracheal tube is forced into the bronchus along the endoscope.

Further, there is a case where a tracheotomy is performed on a subject and the tracheal tube remains inserted therein for a long period of time, to provide respiratory care. In such a case, it is desirable to periodically check the tracheal tube and a state of the bronchus.

CITATION LIST

Patent Literature

[PTL 1] Japanese Patent Application Laid-open Publication No. 2000-70371

SUMMARY OF INVENTION

Technical Problem

However, in the tracheal intubation using an endoscope, it is difficult to secure a space to insert the tracheal tube since it is performed in a state where the endoscope remains inserted. That is, there was a problem that the insertion of the tracheal tube was difficult.

Further, in a conventional art, it was required to insert the endoscope through the mouth or nose once again in order to check the state after the tracheal intubation. That is, the state after the tracheal intubation could not be checked in real time.

The preset invention has been made in view of the above described problem, and an object thereof is to provide a tracheal tube that can be easily inserted into the subject and enables real-time observation of the state after tracheal intubation.

Solution to Problem

A primary aspect of the present invention is a tracheal tube including a hollow tube body, a lumen, and a scope unit. The tube body is configured to be inserted into a subject. The lumen is mounted to the tube body. The scope unit includes a cable portion inserted in the lumen and an imaging optical system mounted to a distal end of the cable portion, the imaging optical system including an imaging device configured to image inside of the subject. Other features of the present invention will become apparent from descriptions of the present specification with reference to the accompanying drawings.

Advantageous Effects of Invention

A tracheal tube according to the present invention can be easily inserted into a subject, and also enables real-time observation of a state after tracheal intubation.

DESCRIPTION OF EMBODIMENT

Summary of Disclosure

Figure 1:
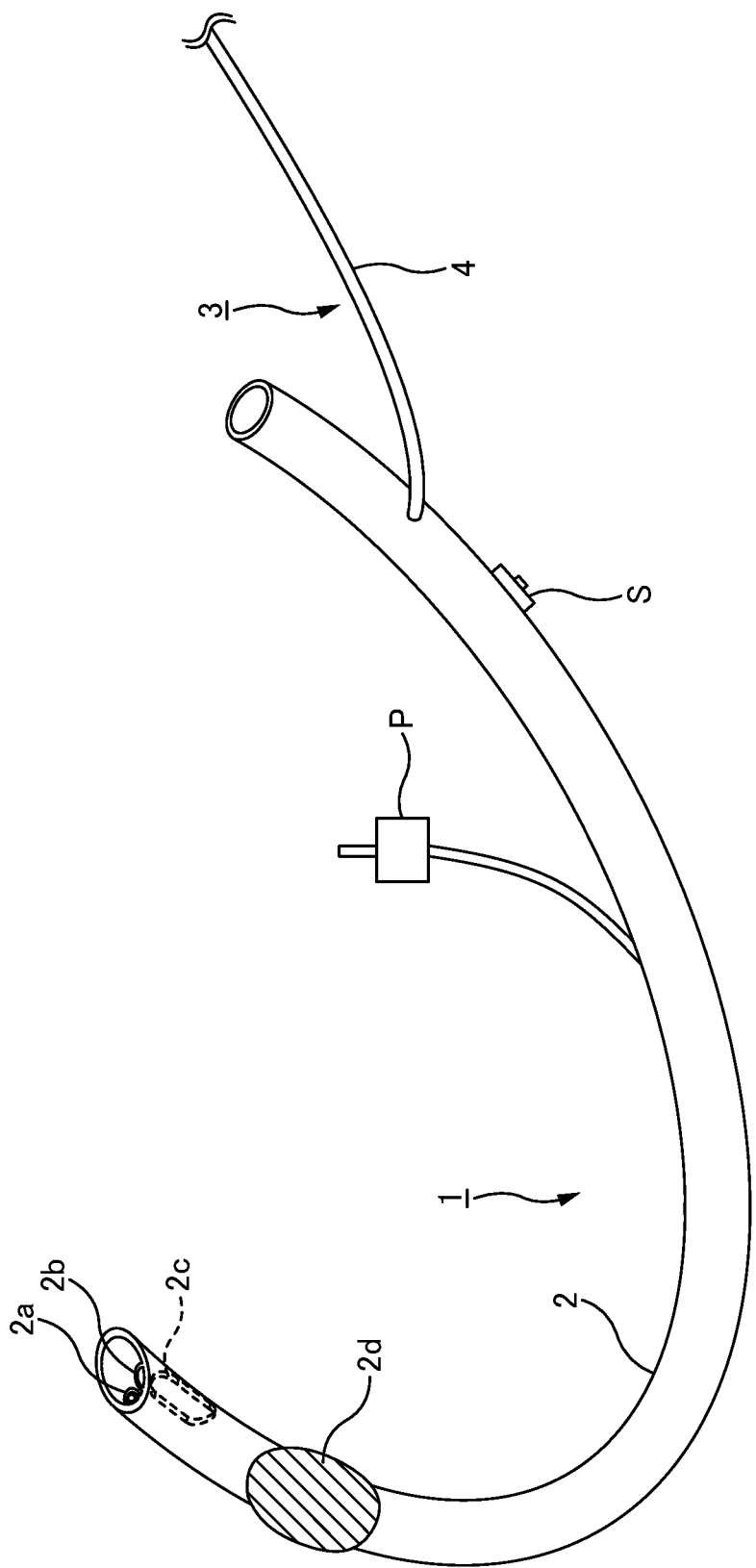
FIG. 1 is a diagram illustrating a tracheal tube according to an embodiment.

At least the following matters will become apparent from descriptions of this specification and of the accompanying drawings.

That is, a tracheal tube will become apparent which includes: a hollow tube body configured to be inserted into a subject; a lumen mounted to the tube body; and a scope unit including a cable portion inserted in the lumen and an imaging optical system mounted to a distal end of the cable portion, the imaging optical system including an imaging device configured to image inside of the subject.

The tracheal tube as such can be easily inserted into the subject, and also enables real-time observation of the state after tracheal intubation.

Further, the tracheal tube will become apparent in which the imaging optical system includes: an imaging device module including the imaging device and an objective lens mounted in front of an imaging surface of the imaging device; and an illumination optical system configured to illuminate the inside of the subject.

With the imaging optical system as such being mounted, the tracheal tube can be easily inserted into the subject, and the state after tracheal intubation can be observed in real time.

Further, the tracheal tube will become apparent in which a distal end surface of the tube body is inclined, and the imaging device module is arranged such that a distal end surface thereof does not protrude more than a longest part of the tube body.

With the tracheal tube as such, the insertion thereof into the subject is facilitated.

Further, the tracheal tube will become apparent in which the illumination optical system includes a light-guide fiber configured to guide a light beam from a light source to the inside of the subject.

Further, the tracheal tube will become apparent in which the light-guide fibers are mounted at least two around the imaging device module, and the emitting surfaces of the light-guide fibers are inclined so that each of optical axes of light beams emitted from the emitting surfaces is directed in a direction away from the distal end surface of the imaging device module.

With the light-guide fibers being configured as such, the influence of halation can be reduced.

Further, the tracheal tube will become apparent in which the emitting surfaces of the light-guide fibers and the distal end surface of the imaging device module protrude from a distal end surface of the lumen.

With the tracheal tube as such, a wide field of view of the imaging device module (objective lens) can be secured. Further, it becomes possible to effectively illuminate the inside of the subject.

Further, the tracheal tube will become apparent in which the distal end surface of the imaging device module protrudes more than the emitting surfaces of the light-guide fibers.

With such an arrangement, the influence of halation can be reduced.

Further, the tracheal tube will become apparent in which the light-guide fibers are plastic optical fibers.

With a plastic optical fiber being used as the light-guide fiber, the manufacturing costs of the tracheal tube can be reduced.

Further, the tracheal tube will become apparent in which the illumination optical system is mounted to the distal end of the cable portion, and includes an LED light source configured to radiate a light beam to the inside of the subject.

With the use of the illumination optical system as such, the diameter of the cable portion can be reduced.

Further, the tracheal tube will become apparent in which the imaging device is a CMOS sensor.

With the CMOS sensor being used as the imaging device, the imaging optical system (the distal end of the cable portion) can be miniaturized.

Further, the tracheal tube will become apparent which includes a suction lumen mounted to the tube body, the suction lumen being configured to suction secretions in the subject, wherein the lumen is mounted at a location away from the suction lumen in the tube body.

Further, the tracheal tube will become apparent in which the lumen is mounted at any location from a location where the suction lumen does not enter a field of view of the imaging optical system to a location opposed to the suction lumen.

Further, the tracheal tube will become apparent in which the tube body includes a Murphy Eye in a vicinity of the distal end of the tube body, and the lumen and the suction lumen are arranged in such a manner as to avoid the Murphy Eye.

With such an arrangement of the lumens, the possibility that observation is disturbed by secretions can be reduced. Further, even in the tracheal tube having the Murphy Eye, the lumen and the suction lumen can be arranged at appropriate locations.

Embodiment

Figure 2:
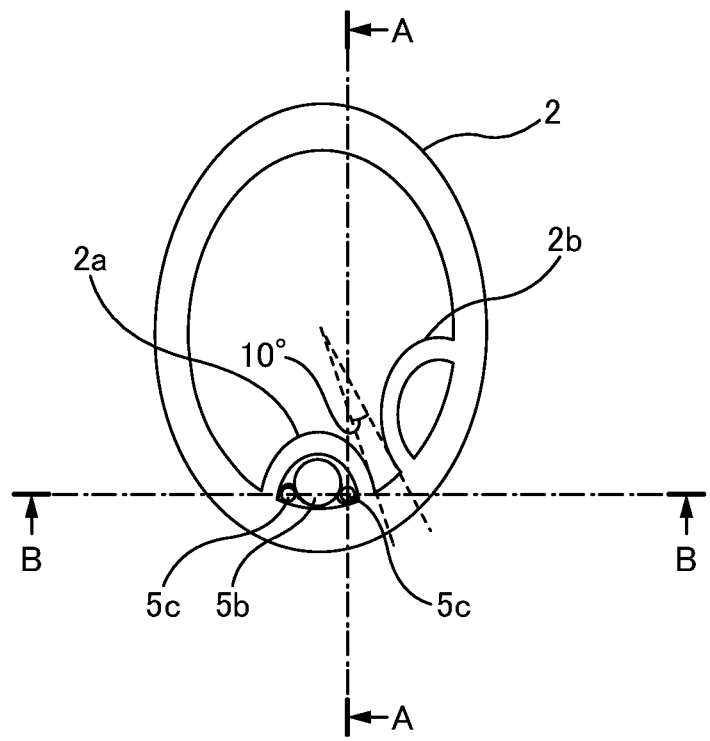
FIG. 2 is a diagram illustrating the tracheal tube according to the embodiment.
Figure 3:
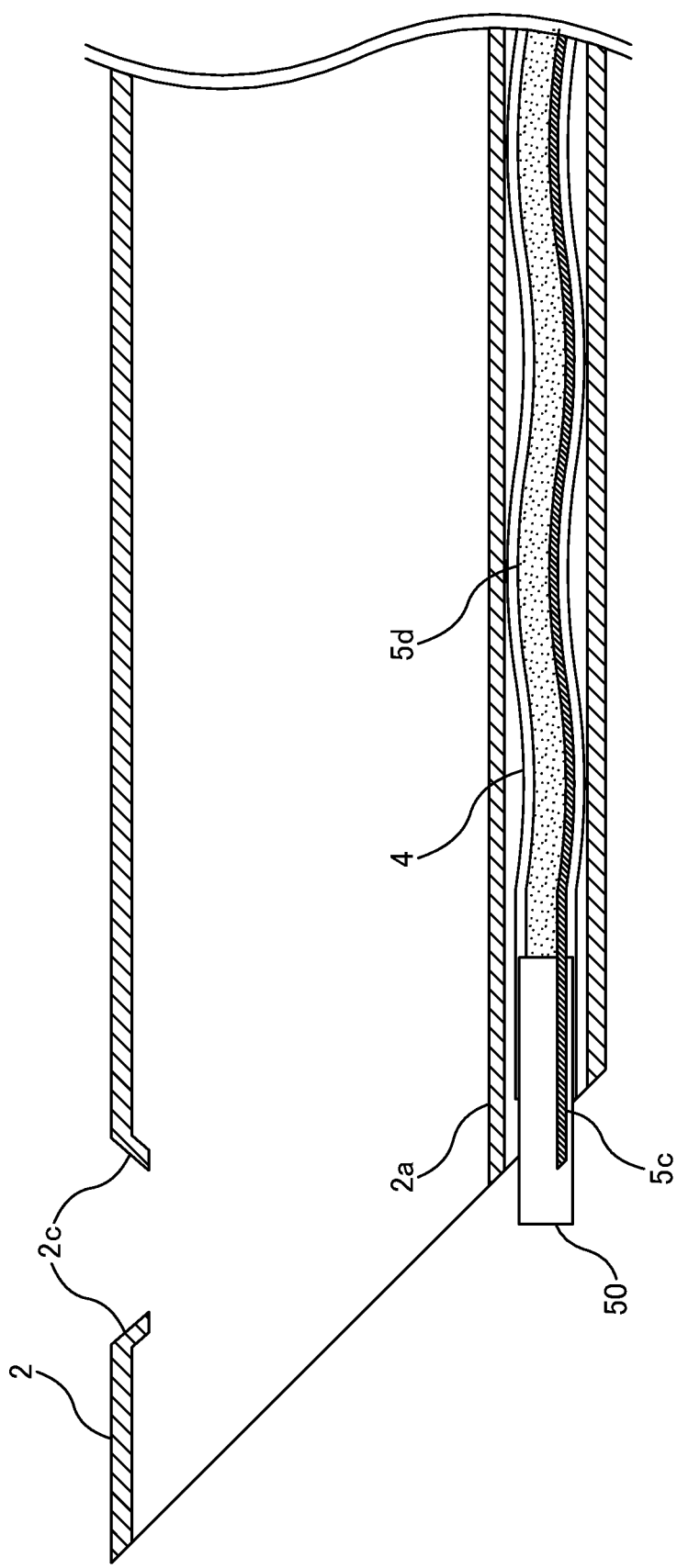
FIG. 3 is a diagram illustrating the tracheal tube according to the embodiment.
Figure 4:
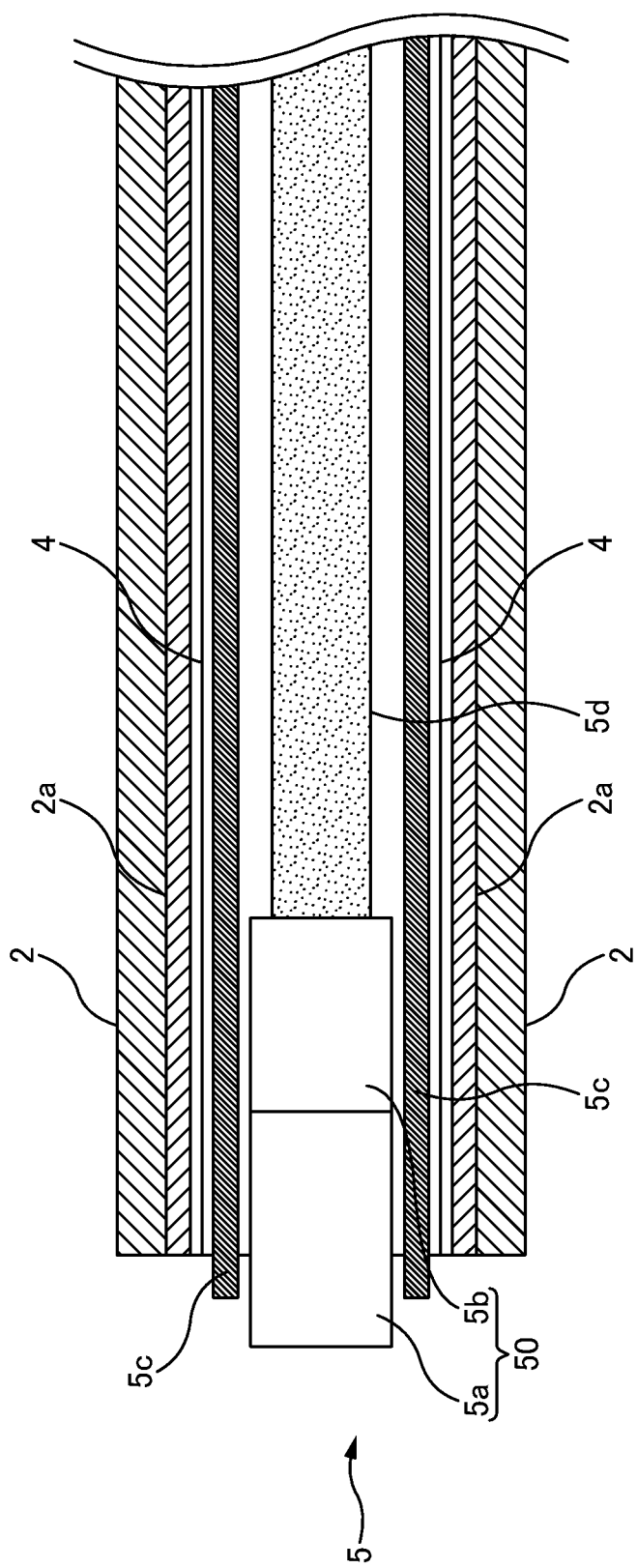
FIG. 4 is a diagram illustrating the tracheal tube according to the embodiment.

The structure of a tracheal tube 1 according to an embodiment will be described with reference to FIGS. 1 to 4. FIG. 1 is an external view illustrating the entire tracheal tube 1. FIG. 2 is a diagram illustrating a distal end surface of the tracheal tube 1. FIG. 3 illustrates a cross-section A-A of FIG. 2 (description of the tracheal tube 1 on the base end side is omitted). FIG. 4 illustrates a cross-section B-B of FIG. 2 (description of the tracheal tube 1 on the base end side is omitted). Note that the scale sizes of the figures are different from one another.

The tracheal tube 1 is medical equipment to maintain a subject's airway. The tracheal tube 1 according to the embodiment includes a tube body 2 and a scope unit 3 (see FIGS. 1 to 4).

<Tube Body>

The tube body 2 is a hollow member inserted into the subject. The tube body 2 includes two lumens (lumen 2a, lumen 2b), a Murphy Eye 2c, and a cuff 2d.

The tube body 2 is formed with, for example, a transparent material, a depth scale (not shown) is marked in the outer surface thereof. Further, the tube body 2 is formed in accordance with the shape of a part (throat to bronchus) into which the tube body 2 is inserted. In the embodiment, the tube body 2 is formed in a curved shape (see FIG. 1). Further, the distal end surface of the tube body 2 protrudes more on the side opposed to the lumen 2a than on the lumen 2a side, in the longitudinal direction of the tube body 2 (see FIG. 3). That is, the distal end surface of the tube body 2 is inclined toward the lumen 2a side. The tube body 2 on the protruding side (on the side opposed to the lumen 2a) is the longest (hereinafter, such a protruding part may be referred to as "the longest part"). On the other hand, the tube body 2 on the base end side is arranged outside the subject and connected via a slip joint (not shown) to a valve varying in type (for example, speaking valve not shown).

The lumens are hollow channels formed inside the tube body 2. In the embodiment, two lumens, which are the lumens 2a and 2b, are mounted.

In the embodiment, the lumen 2a is a dedicated lumen in which the scope unit 3 is inserted. The lumen 2a on the distal end side is opened at the distal end of the tube body 2. The lumen 2a on the base end side is opened at the base end side of the tube body 2.

On the other hand, in the embodiment, the lumen 2b is a suction lumen configured to suction secretions in the subject. The lumen 2b on the distal end side is opened at the distal end of the tube body 2. A suction port S is formed on the base end side of the lumen 2b (tube body 2 on base end side). A suction tube (not shown) or the like is connected to the suction port S to perform suction, thereby being able to suction the secretions in the subject through the lumen 2b.

The distal end surfaces (openings) of the lumens 2a and 2b are flush with the distal end surface of tube body 2 (see FIGS. 1 and 3).

Further, the lumen 2a is mounted at a location away from the lumen 2b. Specifically, the lumen 2a is mounted at any location at least from a location where the lumen 2b does not enter the field of view of an imaging optical system 5 (which will be described later) to a location opposed to the lumen 2b. The location at which the lumen 2b does not enter the field of view of the imaging optical system 5 (which will be described later) represents such a location that the lumens 2a and 2b are away from each other by at least 10 degrees in a cross-section of the tube body 2 (see FIG. 2). As such, the lumen 2a is mounted to be away from the lumen 2b, to reduce the possibility that secretions adhere to the lumen 2a (i.e., the scope unit 3 including the imaging optical system 5 (which will be described later)), even when the secretions are suctioned by the lumen 2b. That is, it is possible to reduce such matters that the observation performed using the scope unit 3 is disturbed by the secretions.

Further, the lumens 2a and 2b (channels) are arranged in such a manner as to avoid the Murphy Eye 2c. In the embodiment, the lumen 2a is mounted at a location opposed to the Murphy Eye 2c. Further, the lumen 2b is arranged at a location away from the lumen 2b by 10 degrees in the cross-section of the tube body 2. That is, the lumens 2a and 2b are arranged in such locations (appropriate locations) where the function of the Murphy Eye 2c is not impaired.

The Murphy Eye 2c is mounted in the vicinity of the distal end part of the tube body 2. The Murphy Eye 2c is a hole to prevent the bronchus from being blocked.

The cuff 2d is mounted at such a location as the periphery of the tube body 2 and not to block the Murphy Eye 2c. The cuff 2d is a member to fix the tube body 2 in the subject. The cuff 2d is in a deflated state when being inserted into or withdrawn from the subject. When the air is started to be supplied by a pilot balloon P, which is mounted outside the subject, the cuff 2d is filled with the air via the flow path (not shown) in the tube body 2. Thus, the cuff 2d is inflated. Then, the inflated cuff 2d comes in contact with a body wall, to fix the tube body 2 to the subject. Note that a suction lumen (lumen different from the lumen 2b) for suctioning the secretions accumulated on the base end side of the cuff 2d in an inflated state may be mounted.

<Scope Unit>

As illustrated in FIGS. 2 to 4, the scope unit 3 includes a cable portion 4 and the imaging optical system 5.

The cable portion 4 is a long tubular member inserted into the lumen 2a. The cable portion 4 is a member that has flexibility and is made of polyethylene and/or the like.

The cable portion 4 inserted into the lumen 2a is bonded and fixed to the tube body 2 at the distal end side and the base end side of the lumen 2a. Further, the cable portion 4 is fixed, in a bend state, inside the lumen 2a (see FIG. 3). Thus, even if an external force is applied to the tracheal tube 1 to deform the tube body 2, the cable portion 4 (scope unit 3) can follow such deformation. As such, the cable portion 4 is fixed, with allowance, inside the lumen 2a, thereby being able to reduce the possibility of occurrence of a break in a wiring portion 5d (signal lines which will be described later) and the like, which is caused by an external force.

The imaging optical system 5 is mounted to (inside) the distal end of the cable portion 4. The imaging optical system 5 is fixed to the cable portion 4 with an adhesive, etc. The imaging optical system 5 includes: an imaging device 5a; an objective lens 5b; a light-guide fiber 5c serving as an illumination optical system, and the wiring portion 5d (see FIG. 4). The imaging optical system 5 is fixed with a resin adhesive, etc., at the distal end of the cable portion 4. The imaging optical system 5 in the embodiment includes at least the imaging device 5a. The imaging device 5a and the objective lens 5b constitute a single unit of an imaging device module 50. Note that the imaging optical system 5 and the cable portion 4 are not necessarily structured in an integrated manner. For example, such a structure is also possible that the distal end part including the imaging device module 50 is bonded and fixed to the distal end of the cable portion 4.

The imaging device 5a is a device configured to image the inside of the subject. For example, a CMOS sensor or a CCD sensor can be used as the imaging device 5a. The CMOS sensor is suitable for miniaturization of the imaging optical system 5 as compared to the CCD sensor.

The objective lens 5b is mounted in front of an imaging surface of the imaging device 5a. The imaging device 5a is configured to capture images of the subject through the objective lens 5b. For example, a GRIN lens can be used as the objective lens 5b. Alternatively, the objective lens 5b may be structured as a lens group in which a plurality of lenses (glass, plastic, etc.) are combined. The objective lens 5b has a viewing angle of, for example, 95 to 120 degrees. A part of the objective lens 5b (imaging device module 50) in the embodiment protrudes from the distal end of the cable portion 4 (see FIGS. 3 and 4).

Further, the objective lens 5b in the embodiment is arranged such that one lens surface thereof (the surface opposite to a lens surface facing the imaging surface) protrudes more than the distal end surface of the lumen 2a (see FIG. 4). That is, the distal end surface of the imaging device module 50 protrudes from the distal end surface of the lumen 2a (see FIGS. 3 and 4). With such an arrangement of the imaging device module 50, at least the lumen 2a does not enter the field of view of the objective lens 5b. Thus, a wide field of view can be secured.

Further, the imaging device module 50 is arranged such that the distal end surface thereof does not protrude more than the longest part of the tube body 2. The tracheal tube 1 as such has less possibility that the imaging device module 50 is stuck when being inserted into the subject. Thus, the insertion of the tracheal tube 1 into the subject is facilitated.

The light-guide fibers 5c are long members each configured to guide a light beam from a light source (not shown). The light beams (illumination light) guided from the light-guide fibers 5c are radiated from the distal end surfaces (emitting surfaces) of the light-guide fibers 5c to the inside of the subject. The light-guide fibers 5c on the base end side are inserted into the cable portion 4, to be connected to the light source (not shown) arranged outside the subject. As the light-guide fibers 5c, a fiber made of multicomponent glass and/or a plastic optical fiber (Plastic Optical Fiber: POF) may be used. The plastic optical fiber is less expensive, and thus the manufacturing costs of the scope unit 3 can be reduced.

In the embodiment, two light-guide fibers 5c are mounted across the imaging device module 50 (see FIGS. 2 and 4). Further, the light-guide fibers 5c are arranged such that the emitting surfaces thereof protrude more than the distal end surface of the lumen 2a (see FIGS. 3 and 4). With such an arrangement, the illumination light is not blocked by the lumen 2a. Thus, it is possible to effectively illuminate the inside of the subject.

Further, the emitting surfaces of the light-guide fibers 5c are inclined so that each of the optical axes of emitted light beams is directed in a direction away from the distal end surface of the imaging device module 50 (lens surface of the objective lens 5b) (see FIG. 3). With the emitting surfaces of the light-guide fibers 5c being inclined as such, the optical axes of the light beams emitted from the emitting surfaces is in a direction or directions away from the distal end surface of the imaging device module 50. That is, it becomes hard for the light beams emitted from the emitting surfaces to enter the distal end surface of the imaging device module 50. This makes it possible to reduce the influence of halation caused by the illumination light. Note that the inclination of the emitting surfaces of the light-guide fibers 5c is not limited to that corresponding to the shape illustrated in FIG. 3 (inclined downward with respect to the longitudinal direction of the light-guide fibers 5c). For example, the emitting surfaces may be inclined outward with respect to the longitudinal direction of the light-guide fibers 5c (in the opposite side of the imaging device module 50; toward the front as viewed on the paper of FIG. 3).

Further, the imaging device module 50 and the light-guide fibers 5c are arranged such that the distal end surface of the imaging device module 50 protrudes more than the emitting surfaces of the light-guide fibers 5c (see FIGS. 3 and 4). Such an arrangement of the imaging device module 50 and the light-guide fibers 5c makes it possible to reduce the direct entrance of the light beams from the light-guide fibers 5c into the imaging device module 50. Thus, it becomes possible to further reduce the influence of halation caused by the light beams (illumination light) from the light-guide fibers 5c.

The wiring portion 5d is a unit formed by covering a plurality of signal lines with an outer sheath. The signal lines are lines for transmitting a drive signal (and drive power) for driving the imaging device 5a and an imaging signal from the imaging device 5a (a signal obtained by converting a captured image into an electrical signal). The distal ends of the signal lines are connected to the imaging device 5a. The signal lines on the base end side are inserted in the cable portion 4, to be connected to a processor (not shown) through a connector (not shown). The processor (not shown) is a device arranged outside the subject. The processor (not shown) has functions of processing the imaging signal to form an image and supplying the drive power for the imaging device 5a. Note that the signal lines and the imaging device 5a can be electrically connected through an FPC board or the like.

The tracheal tube 1 as such can be inserted into the subject while checking an actual image. Thus, it is possible to reliably insert the tracheal tube 1 with respect to the bronchus without inserting an endoscope or the like in advance. Further, even after the insertion, it is possible to observe a state after tracheal intubation in real time using the scope unit 3. Thus, since it is unnecessary to insert an endoscope in every observation, time and effort for procedures performed by a doctor, etc., can be saved and also the burden on a patient can be lightened.

Modified Example 1

The illumination optical system is not limited to the light-guide fibers 5c. For example, an LED light source can be used as the illumination optical system. The LED light source is mounted to the distal end of the cable portion 4, and is configured to radiate light to the inside of a subject. The LED light source is configured to be supplied with drive power through the wiring portion 5d (signal lines), to radiate light. In this case, since the light-guide fibers 5c are unnecessary, the diameter of the cable portion 4 can be reduced.

Modified Example 2

The above embodiment describes a configuration including two lumens (lumens 2a and 2b), but the number of lumens is not limited thereto. For example, the tube body 2 may include only a single lumen. In this case, the scope unit 3 is arranged in the single lumen.

Further, it is unnecessary to provide a dedicated lumen for the scope unit 3 to be inserted thereto, as in the case of the lumen 2a. For example, the lumen 2b (suction lumen) may be used for the scope unit 3.

Further, a lumen other than the lumen 2a which is mounted to the tube body 2 (lumen 2b in the above embodiment) is not limited to the suction lumen. For example, a cleaning lumen for discharging saline, etc., to clean the distal end part of the tracheal tube 1 may be mounted. The cleaning lumen may be mounted in the vicinity of the lumen (lumen 2a) in which the scope unit 3 is arranged, unlike in the case of the suction lumen. For example, the scope unit 3 (imaging device module 50, etc.) may get dirty with the secretions in the subject. In this case, the cleaning lumen discharges saline, thereby being able to eliminate dirt from the scope unit 3.

REFERENCE SIGNS LIST 1 tracheal tube
2 tube body
2a, 2b lumen
2c Murphy Eye
2d cuff
3 scope unit
4 cable portion
5 imaging optical system
5a imaging device
5b objective lens
5c light-guide fiber
5d wiring portion
P pilot balloon
S suction port

The invention claimed is:
1. A tracheal tube comprising:
a hollow tube body configured to be inserted into a subject;
a lumen mounted to the tube body; and
a scope unit including a cable portion inserted in the lumen and an imaging optical system mounted to a distal end of the cable portion, the imaging optical system including an imaging device configured to image an inside of the subject,
the imaging optical system including
an imaging device module including the imaging device and an objective lens mounted in front of an imaging surface of the imaging device, and
an illumination optical system configured to illuminate the inside of the subject,
the illumination optical system including at least two light-guide fibers configured to guide a light beam from a light source to the inside of the subject,
the at least two light-guide fibers being mounted around the imaging device module,
the at least two light-guide fibers having obliquely cut flat emitting surfaces that are inclined with respect to a light-guide fiber optical axis,
the emitting surfaces are arranged such that an optical axis of each light beam emitted from the emitting surfaces is directed in a direction away from a distal end surface of the imaging device module, to reduce entrance of each light beam emitted from the emitting surfaces into the distal end surface of the imaging device module,
the two light guide fibers are mounted across the imaging device module and;
the cable portion of the scope unit is bonded anal fixed to the tube body at a proximal end side and a distal end side of the lumen.
2. The tracheal tube according to claim 1, wherein
a distal end surface of the tube body is inclined, and
the imaging device module is arranged such that the distal end surface thereof does not protrude more than a longest part of the tube body.
3. The tracheal tube according to claim 1, wherein
emitting surfaces of the light-guide fibers and the distal end surface of the imaging device module protrude from a distal end surface of the lumen.

4. The tracheal tube according to claim 1, wherein
the distal end surface of the imaging device module protrudes more than emitting surfaces of the light-guide fibers.

5. The tracheal tube according to claim 1, wherein the light-guide fibers are plastic optical fibers.

6. The tracheal tube according to claim 1, wherein the imaging device is a CMOS sensor.

7. The tracheal tube according to claim 1, comprising
a suction lumen mounted to the tube body, the suction lumen being configured to suction secretions in the subject, wherein
the lumen is mounted at a location away from the suction lumen in the tube body.

8. The tracheal tube according to claim 7, wherein
the lumen is mounted at any location from a location where
the lumen and the suction lumen are away from each other by at least 10 degrees to a location opposed to the suction lumen in a cross-section of the tube body.

9. The tracheal tube according to claim 7, wherein
the tube body includes a Murphy Eye in a vicinity of distal end of the tube body, and
the lumen and the suction lumen are arranged at a location at which the Murphy Eye is not mounted.

* * * * *